US011123391B2

(12) United States Patent
Toh et al.

(10) Patent No.: US 11,123,391 B2
(45) Date of Patent: Sep. 21, 2021

(54) NASAL COMPOSITION

(71) Applicant: INQPHARM GROUP SDN BHD, Kuala Lumpur (MY)

(72) Inventors: Janice Pei Yin Toh, Kuala Lumpur (MY); Qingwen Chen, Kuala Lumpur (MY); Bee Kwan Tan, Kuala Lumpur (MY); Volker Schehlmann, Kuala Lumpur (MY); Audrey Li Chin Chew, Kuala Lumpur (MY); Albrecht Jörg Matthias Miller, Kuala Lumpur (MY)

(73) Assignee: INQPHARM GROUP SDN BHD, Kuala Lumpur (MY)

( * ) Notice: Subject to any disclaimer, the term of this patent is extended or adjusted under 35 U.S.C. 154(b) by 475 days.

(21) Appl. No.: 15/749,745

(22) PCT Filed: Aug. 3, 2016

(86) PCT No.: PCT/MY2016/000046
§ 371 (c)(1),
(2) Date: Feb. 1, 2018

(87) PCT Pub. No.: WO2017/023162
PCT Pub. Date: Feb. 9, 2017

(65) Prior Publication Data
US 2018/0228857 A1    Aug. 16, 2018

(30) Foreign Application Priority Data

Aug. 4, 2015 (MY) .......................... PI2015702548
Jun. 28, 2016 (MY) .......................... PI2016702385

(51) Int. Cl.
| *A61K 36/535* | (2006.01) |
| *A61K 9/00* | (2006.01) |
| *A61K 36/71* | (2006.01) |
| *A61P 37/08* | (2006.01) |
| *A61K 9/12* | (2006.01) |
| *A61K 47/10* | (2017.01) |
| *A61K 47/44* | (2017.01) |
| *A61K 47/36* | (2006.01) |

(52) U.S. Cl.
CPC .......... *A61K 36/535* (2013.01); *A61K 9/0043* (2013.01); *A61K 9/12* (2013.01); *A61K 36/71* (2013.01); *A61P 37/08* (2018.01); *A61K 47/10* (2013.01); *A61K 47/36* (2013.01); *A61K 47/44* (2013.01)

(58) Field of Classification Search
CPC ...... A61K 36/534; A61K 36/53; A61K 36/28; A61K 36/537; A61K 36/752; A61K 2300/00; A61K 36/535; A61K 36/71; A61K 47/10; A61K 47/36; A61K 47/44; A61K 9/0043; A61K 9/12; A61P 37/08
USPC ................ 424/764, 776, 747, 746, 736, 765
See application file for complete search history.

(56) References Cited

U.S. PATENT DOCUMENTS

| 3,691,281 | A | 9/1972 | Battista | |
| 2007/0082071 | A1* | 4/2007 | Willimann | A61K 47/18 424/727 |
| 2008/0206161 | A1 | 8/2008 | Tamarkin et al. | |
| 2012/0100234 | A1* | 4/2012 | Kulesza | A61K 31/4015 424/766 |
| 2015/0004266 | A1 | 1/2015 | Babish et al. | |

FOREIGN PATENT DOCUMENTS

| EP | 1 343 472 B1 | 5/2006 | |
| WO | 2002/051379 A2 | 7/2002 | |
| WO | 2012/107356 A1 | 8/2012 | |
| WO | WO-2012107356 A1 * | 8/2012 | ........... A61K 9/0043 |
| WO | 2012/119261 A1 | 9/2012 | |

OTHER PUBLICATIONS

International Search Report with Written Opinion corresponding to International Patent Application No. PCT/MY2016/000046, dated Nov. 14, 2016.

* cited by examiner

*Primary Examiner* — Aaron J Kosar
(74) *Attorney, Agent, or Firm* — Pauley Erickson & Swanson

(57) ABSTRACT

The present invention relates to a nasal composition comprising an anti-allergic oil derived from plant; and an oil-based barrier-forming preparation. The composition may be used in preventing and/or treating allergic disorders of the nasal cavity, including seasonal allergic rhinitis (hay fever) and perennial allergic rhinitis.

22 Claims, 4 Drawing Sheets

NASAL COMPOSITION

RELATED APPLICATIONS

This application is a 35 U.S.C. § 371 filing of International Patent Application No. PCT/MY2016/000046, filed Aug. 3, 2016, which claims priority to Malaysian Patent Application No. PI2016702385, filed Jun. 28, 2016, and Malaysian Patent Application No. PI2015702548, filed Aug. 4, 2015, the entire disclosures of which are hereby incorporated herein by reference in their entirety.

TECHNICAL FIELD OF THE INVENTION

The present invention relates to a nasal composition. In particular, the present invention relates to a nasal composition that may be used to inhibit activation of mast cells. More particularly, the present invention relates to an anti-allergic nasal composition with efficacy for use in preventing and/or treating allergic disorders of the nasal cavity, such as seasonal allergic rhinitis and perennial allergic rhinitis.

BACKGROUND OF THE INVENTION

The causes of allergic rhinitis, a disorder of the nasal mucous membrane, are in principle known. Mainly, an immune reaction takes place, which, due to specific mediators, incurs local and systemic effects in the patient. Primarily, tissue mast cells are attacked, which feature, inter alia, non-specific and specific receptors in the outer cell membrane (for immunoglobulin E, for example). The bonding of allergens to these receptors leads to the release of histamine and other inflammatory mediators, such as leukotrienes and prostaglandins. As a consequence of the effect of these mediators, the musculature of the vessels becomes slack, the permeability of the vessels and the membrane increases, and constriction of the bronchial musculature occurs. The symptoms of allergic rhinitis follow from these reactions: Local rubor and swelling of the nasal mucosa and of the conjunctiva, as well as increased emergence of fluid into the tissue and resultant increased secretion in the nose and eyes. Systemic effects may also occur, such as hypotonic states in the cardiovascular system.

This cascade of effects is triggered primarily by exogenic agents, such as pollen, house dust, animal hair, foodstuff constituents, pharmaceutical preparations or mites, or by antibodies which were themselves formed in the organism as a reaction to pollen or other foreign substances. This is a disorder which is very frequently encountered: A survey conducted in 1992/1993 of 2,400 school students indicated that 13.5% had suffered from hayfever in the previous year. Pollen allergies are the leaders in atopic disorders.

The therapy for allergic rhinitis is based on three main principles: Allergen restriction, medicamentous therapy (symptomatic only), and specific immunotherapy (hyposensitisation).

Allergen restriction, which takes causal effect, is intended to avoid or reduce the exposure of the patient to allergens, in order to avoid contact with mast cells. This includes measures in the everyday conduct of life, such as keeping windows and doors closed, fitting pollen filters in air-conditioning systems, no sports practised in the open air, holidays in other climatic zones, etc. This however requires a high level of compliance on the part of the patient and his surroundings. The method is effective prophylactically, especially.

Medicamentous therapy is considerably elaborate and expensive, and as a general rule the attempt must also be made to reduce allergen exposure. Oversensitivity reactions are possible. The causally effective hyposensitisation requires in particular a high level of diagnostic effort, is elaborate, is a burden on the patient (because of the regular injections over an extended period) and does not demonstrate any sustained or reliably reproducible effect.

Preparations which make additional forms of therapy possible, which show low side-effects and which are effective in a simple manner (in particular prophylactically), and which make possible allergen restriction have been provided and described in European Patent No. EP1343472. This patent document discloses a thixotropic preparation, in particular a thixotropic nasal spray, free of active substance, for use in the therapeutic treatment of the human or animal body, in particular for use in the therapeutic treatment of nasal disorders, in particular allergic rhinitis. As the thixotropic preparation is capable of forming a physical barrier in the nasal cavity which prevents the entrance of allergens thereinto, this composition is effective in reducing the exposure of the subject to allergen, and avoiding its contact with mast cells. However, this thixotropic preparation may not be as effective when the disruptive rhinitis symptoms have been present.

Therefore, there is an ongoing need for further anti-allergic compositions, for example, with enhanced prophylactic and/or therapeutic effects, for allergic disorders of the nasal cavity, such as allergic rhinitis including pollinosis.

SUMMARY OF THE INVENTION

The present invention aims to provide a nasal composition having a specific combination of active ingredients, which includes a natural anti-allergic substance. In certain embodiments, the nasal composition of the present invention aims to provide an improved performance of the product, particularly its barrier function as well as sprayability and improved spray pattern, and thus resulting in an enhanced efficacy in prophylaxis and treatments of allergic disorders of the nasal cavity, including seasonal allergic rhinitis and perennial allergic rhinitis.

In certain embodiments, the nasal composition of the present invention aims to provide a composition having a specific combination of active ingredients, which act synergistically, to provide an enhanced anti-allergic effect. In certain embodiments, the nasal composition of the present invention aims to inhibit mast cell activation and/or mast cell degranulation and/or release of histamine from mast cells.

According to a first aspect, there is provided a nasal composition comprising an anti-allergic oil derived from plant and an oil-based barrier-forming preparation.

The anti-allergic oil used in the nasal composition can be derived from the plant of *Perilla* spp., *Nigella* spp., *Urtica* spp. *Astragalus* spp., *Petasites* spp., *Citrus* spp., *Uncaria* spp., *Lavandula* spp., *Mentha* spp., *Eucalyptus* spp., *Matricaria* spp., *Rosmarinus* spp., *Curcuma* spp., *Allium* spp., or a combination of any two or more thereof.

The anti-allergic oil as set forth in the preceding description can be obtained from the seed, root, leaf, or whole plant parts of the plant.

The oil-based barrier-forming preparation of the composition can contain three components, which are an oily component, one or more gel formers, for example, gel formers for a thixotropic gel, and an aqueous base. The first component, which is the oily component, can be a hydrocarbon, a plant oil, a vegetable oil or hydrated, polyoxyethylated or polyoxy- or hydrated polyoxy or fractionated derivatives thereof, or a combination of any two or more thereof. Preferably, the oily component is sesame oil.

The anti-allergic oil and the oily component can be present in a weight ratio range of 1-10:10-1.

In certain embodiments, the anti-allergic oil and the oily component are preferably distinct species, i.e., the nasal composition does not contain the same oil as both anti-allergic oil and the oily component.

The second component of the oil-based barrier-forming preparation of the composition is the one or more gel formers, for example, one or more gel formers for a thixotropic gel, which can be selected from the group consisting of organic suspension media and inorganic suspension media, or a combination thereof. Preferably, the one or more gel formers for thixotropic gel can contain xanthan gum, bentonite, glycerol monostearate or a combination of any two or more thereof.

The third component, which is the aqueous base, can be water, or water with stabilising additives.

In certain embodiments, the oil-based barrier-forming preparation of the nasal composition is an oil-in-water emulsion or microemulsion.

The nasal composition can be prepared in the form of a nasal spray. Preferably, the nasal composition can provide a substantially annular or circular spray pattern, as may be determined in accordance with the sprayability test method described herein. Preferably, the area of coverage of the spray pattern formed in the nasal cavity is in a range of about 70% and 95%.

More preferably, the substantially annular spray pattern has an annular ring width range of 0.5 cm to 12.0 cm, with a distance between an origin of spray to an impinged surface of 0.1 cm to 10.0 cm. In certain embodiments, the substantially annular spray pattern has an annular ring width range of 0.5 cm to 12.0 cm, with a distance between an origin of spray to an impinged surface 7.0 cm. In such embodiments, the unit dose per spray may be from about 120 µl to about 160 µl.

According to a second aspect, there is provided a pharmaceutical composition comprising a composition according to the first aspect and a pharmaceutically acceptable carrier, excipient, diluent and/or additive. The pharmaceutically acceptable carrier, excipient and/or diluent for use in the pharmaceutical composition can be selected from the group consisting of binders, surfactants, preservatives, colourants, flavouring substances, pH regulators, regulators of the osmotic activity and salt-forming groups.

According to a third aspect, there is provided a nasal composition according to the first aspect or a pharmaceutical composition according to the second aspect for use in a therapeutic method of inhibiting mast cell activation. According to a further aspect, there is provided a therapeutic method for inhibiting mast cell activation, comprising contacting the mast cells with a nasal composition according to the first aspect or a pharmaceutical composition according to the second aspect.

According to a fourth aspect, there is provided a nasal composition according to the first aspect or a pharmaceutical composition according to the second aspect for use in a therapeutic method of inhibiting mast cell degranulation. According to a further aspect, there is provided a therapeutic method for inhibiting mast cell degranulation, comprising contacting the mast cells with a nasal composition according to the first aspect or a pharmaceutical composition according to the second aspect.

According to a fifth aspect, there is provided a nasal composition according to the first aspect or a pharmaceutical composition according to the second aspect for use in a therapeutic method of inhibiting release of histamine from mast cells. According to a further aspect, there is provided a therapeutic method for inhibiting release of histamine from mast cells, comprising contacting the mast cells with a nasal composition according to the first aspect or a pharmaceutical composition according to the second aspect.

According to a sixth aspect, there is provided a nasal composition according to the first aspect or a pharmaceutical composition according to the second aspect for use in preventing and/or treating allergic disorders of the nasal cavity, including seasonal allergic rhinitis and perennial allergic rhinitis.

According to a seventh aspect, there is provided a therapeutic method for inhibiting mast cell activation comprising administering a nasal composition according to the first aspect or a pharmaceutical composition according to the second aspect to the mast cells.

According to an eighth aspect, there is provided a therapeutic method for inhibiting mast cell degranulation comprising administering a nasal composition according to the first aspect or a pharmaceutical composition according to the second aspect to the mast cells.

According to a ninth aspect, there is provided a therapeutic method for inhibiting release of histamine from mast cells comprising administering a nasal composition according to the first aspect or a pharmaceutical composition according to the second aspect to the mast cells.

In certain embodiments of any aspect of the present invention, the concentration of histamine in the tissue of a subject is reduced by at least about 20% after administration of a nasal composition according to the first aspect or a pharmaceutical composition according to the second aspect. In certain embodiments, the concentration of histamine in the tissue of a subject is reduced by at least about 40% after administration of a nasal composition according to the first aspect or a pharmaceutical composition according to the second aspect. In certain embodiments, the concentration of histamine in the tissue of a subject is reduced by at least about 50% after administration of a nasal composition according to the first aspect or a pharmaceutical composition according to the second aspect.

According to a tenth aspect, there is provided a method for preventing and/or treating allergic disorders of the nasal cavity, including seasonal allergic rhinitis and perennial allergic rhinitis, in a subject comprising administering to the subject an effective amount of a nasal composition according to the first aspect or a pharmaceutical composition according to the second aspect.

According to a eleventh aspect, there is provided the use of an anti-allergic oil derived from plant and an oil-based barrier-forming preparation in the manufacture of a medicament, pharmaceutical composition, or nasal composition for preventing and/or treating allergic disorders of the nasal cavity, including seasonal allergic rhinitis and perennial allergic rhinitis.

DETAILED DESCRIPTION OF THE INVENTION

Figure 1A:
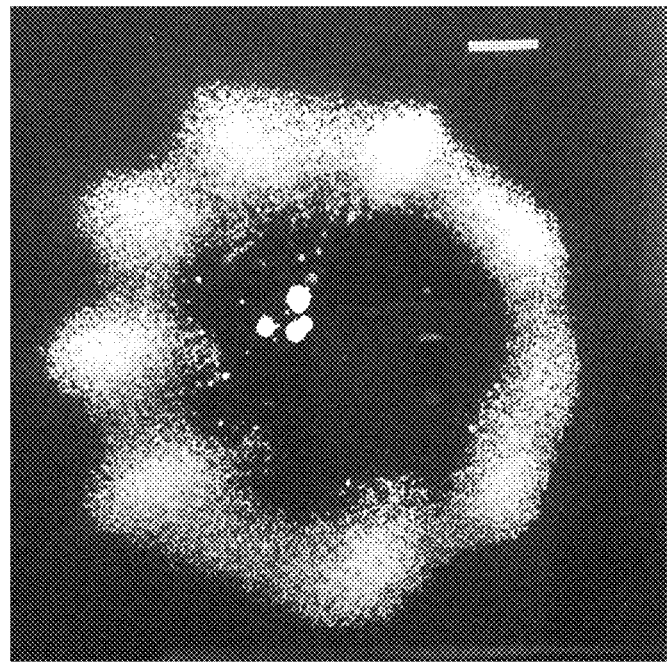
FIGS. 1A-1E are a set of photographs of the spray patterns formed by the nasal composition as described in one of the preferred embodiments of the present invention, in which different ratios of the anti-allergic oil and the oily component are used: sesame oil only, without anti-allergic oil (FIG. 1A); *perilla* oil and sesame oil in a weight ratio of 1:3 (FIG. 1B); *perilla* oil and sesame oil in a weight ratio of 1:1 (FIG. 1C); *perilla* oil and sesame oil in a weight ratio of 3:1 (FIG. 1D); and *perilla* oil as both the anti-allergic oil and the oily component (FIG. 1E).
Figure 1B:
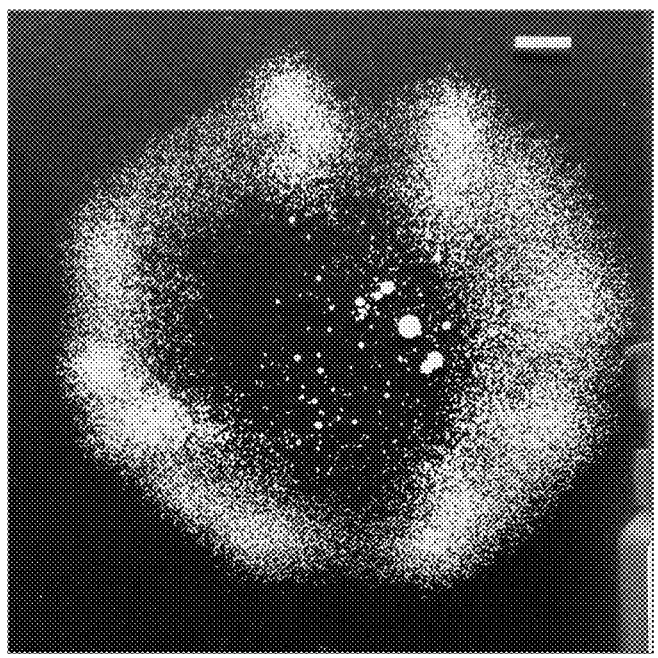
Figure 1C:
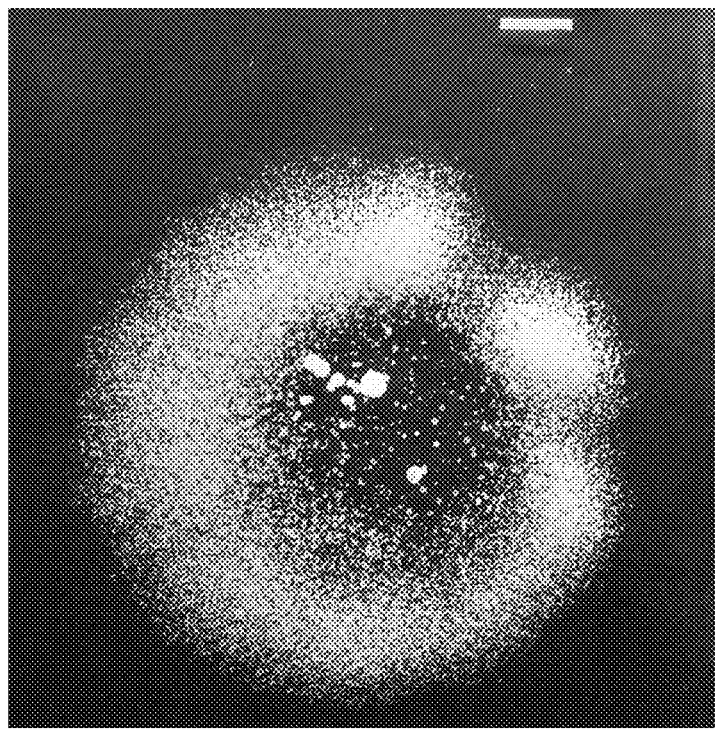
Figure 1D:
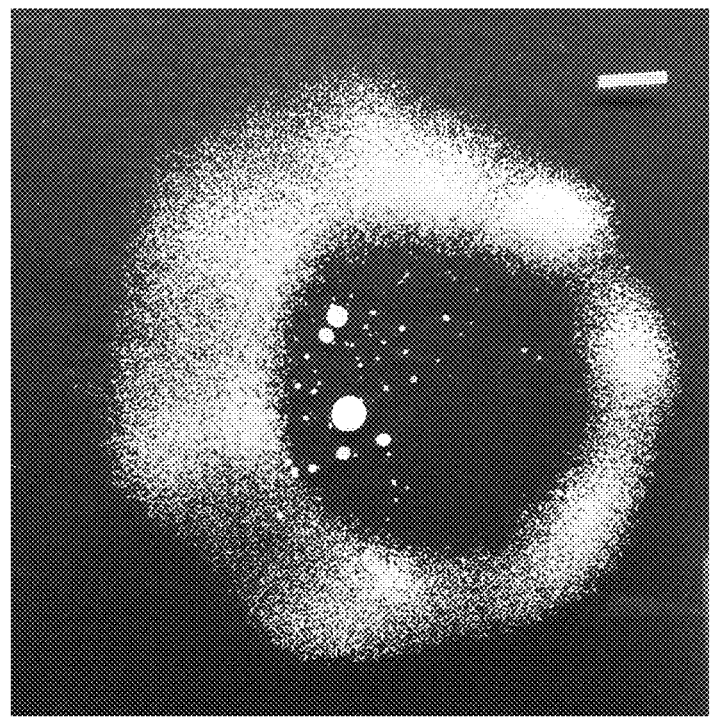
Figure 1E:
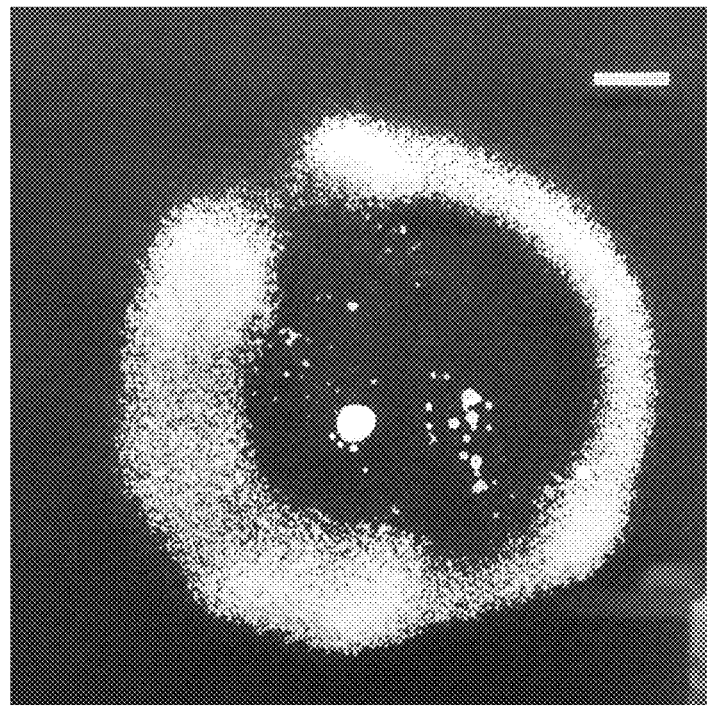

Hereinafter, the invention shall be described according to preferred embodiments of the present invention and by referring to the accompanying description and drawings. However, it is to be understood that limiting the description to the preferred embodiments of the invention is merely to facilitate discussion of the present invention and it is envisioned that those skilled in the art may devise various modifications without departing from the scope of the appended claim.

The terms generally used hereinbefore and hereinafter have for preference the meanings indicated below, unless indicated otherwise, whereby more specific meanings may be used independently of one another in preferred embodiments of the present inventions instead of the general definitions, these more specific significances describing especially preferred embodiments of the invention.

Where the term "at least one" or "one or more" occurs hereinbefore and hereinafter, this signifies in particular one to ten, for preference one to three, and in particular one or, further, two of the features enumerated, such as components. Where ranges are indicated, such as weight percentage ranges, these include the limit values indicated; thus, for example, "between X and Y" signifies "from and including X up to and including Y".

The term "product" is to be understood to mean in particular a pharmaceutical product in the sense of a formulation, for preference a pharmaceutical product, whereby this term is not restricted to pharmaceutical products suitable for registration, or a medical product or fictitious pharmaceuticals. The "product" is also referred to in particular a nutraceutical product in the sense of a formulation, for preference a nutraceutical product in the category of medical device, natural-based product or the like.

The term "anti-allergic" is to be understood to relate to an agent or measure that prevents, inhibits, or alleviates an allergic reaction.

The term "thixotropic preparation" is to be understood to mean such that feature, when subjected to shear forces (shaking, pressing through a nozzle, stirring, or the like), a low viscosity (sol state), suitable in particular for use as nose drops or in particular as a nasal spray, for example in the range from 50-300 Pa·S in low shear and <150 Pa·S in high shear. In an example of stability test, in a state of rest, the viscosity range can range from 1-15 Pa·S, e.g. 8-10 Pa·S. The measurement is effected by means of a rotation viscometer, and the readouts may be affected by the difference between equipment and methods.

The term "therapeutic treatment", also includes prophylaxis and the alleviation of symptoms in a subject, although not cosmetic treatments. This relates to therapeutic treatment, and in particular prophylaxis or alleviation, of disorders of the nasal cavity relating to mast cell activation and/or mast cell degranulation. This relates to therapeutic treatment, and in particular prophylaxis or alleviation, of disorders of the upper nasal passages, in particular of the nasopharynx and the nasal cavity (hereinbefore and hereinafter "nasal disorders"), and in particular for the therapy and prophylaxis of allergic processes located therein, such as, in particular, allergic rhinitis, including seasonal allergic rhinitis (which is also known as pollinosis), as well as perennial allergic rhinitis caused by house dust or animal hair allergy.

The term "sprayability", with reference to the nasal or pharmaceutical compositions of the present invention, means that the nasal or pharmaceutical composition is capable of being administered by spraying. In certain embodiments, "sprayability" means that the spray pattern formed has an annular ring width range of 0.5 cm to 12 cm, with a distance between an origin of spray to an impinged surface of 0.1 cm to 10 cm, for example 7 cm, wherein the impinged surface is a planar surface held vertically above the origin of spray, as may be determined in accordance with the sprayability test method described herein.

The components referred to hereinbefore and hereinafter are in particular selected from among those such as are listed in pharmacopoeia, e.g. in the US Pharmacopoeia National Formulary, the Pharmacopoea Europea, the Pharmacopoea Helvetica, the British Pharmacopoeia, or the German Pharmacopoeia, or supplements, such as by way of decrees.

The present invention relates to a nasal composition comprising an anti-allergic oil derived from plant and an oil-based barrier-forming preparation.

The oil-based barrier-forming preparation of the composition is capable of providing a positive effect against nasal disorders, in particular allergic rhinitis, by providing a "mechanical" barrier. Without wishing to be bound solely to this explanation, it appears that the effect against the allergens that cause allergic rhinitis is based on a "mechanical" blocking function (in particular due to the oily components contained and/or the viscosity of the gel) which can be provided by the barrier-forming preparation, the allergens thus being no longer able to proliferate directly on the nasal mucous membrane due to the largely uniform distribution of the gel on the mucous membrane, and therefore do not come in contact with the mast cells. As a result, the allergic reactions described hereinbefore are eliminated entirely or diminished. The blocking function takes place directly after administration.

The anti-allergic oil used in the nasal composition is preferably a natural substance possessing anti-allergic properties. This anti-allergic oil can be derived from the plant of *Perilla* spp. (e.g. *Perilla frutescens* which is also known as perilla, Chinese basil, beefsteak, etc), *Nigella* spp. (e.g. *Nigella sativa* which is also known as black cumin, black caraway or fennel seed), *Urtica* spp. (e.g. nettle), *Astragalus* spp. (e.g. milk vetch), *Petasites* spp. (e.g. butterbur), *Citrus* spp. (e.g. lemon), *Uncaria* spp. (e.g. Cat's claw), *Lavandula* spp. (e.g. lavender), *Mentha* spp. (e.g. peppermint), *Eucalyptus* spp. (e.g. *Eucalyptus globulus* which is also known as Tasmanian blue gum, southern blue gum or blue gum), *Matricaria* spp. (e.g. German chamomile), *Rosmarinus* spp. (e.g. rosemary), *Curcuma* spp. (e.g. turmeric), *Allium* spp. (e.g. garlic), or a combination of any two or more thereof.

The anti-allergic oil as set forth in the preceding description can be obtained from the seed, root, leaf, or whole plant parts of the plant as listed in the preceding description. For example, the anti-allergic oil is *perilla* oil derived from seed of the plant of *Perilla* spp., and/or *nigella* oil derived from seed of the plant of *Nigella* spp.

The anti-allergic oil added to or combined with the oil-based barrier-forming preparation is capable of improving the performance in barrier-forming, by controlling symptoms that can disrupt stability of the gel barrier. Furthermore, the inclusion of the plant-derived oil to the oil-based barrier-forming preparation is also capable of enhancing the product characteristics, particularly its sprayability, by altering the physical and chemical properties of the oil-based barrier-forming preparation.

The oil-based barrier-forming preparation of the composition can contain three components, which are an oily component, one or more gel formers, for example, one or more gel formers for a thixotropic gel, and an aqueous base.

The first component, which is the oily component, can be a hydrocarbon, a plant oil, a vegetable oil or hydrated, polyoxyethylated or polyoxy- or hydrated polyoxy or fractionated derivatives thereof, or a combination of any two or more thereof.

The examples of hydrocarbons which are suitable to be used as an oily component of the present invention include mineral oils, in particular paraffin, paraffin oil (in particular white paraffin oil, low-viscosity or in a broader embodiment high-viscosity paraffin oil), purcellin oil, perhydrosqualene, hard paraffin or vaseline, whereby low-viscosity paraffin oil is highly preferred. On the other hand, vegetable oils such as spearmint oil, almond oil, groundnut oil, wheatgerm oil, rape oil, linseed oil, apricot oil, walnut oil, palm oil, pistachio oil, sesame oil, poppyseed oil, pine oil, castor oil, soya oil, avocado oil, cocoa oil, hazelnut oil, olive oil, grapeseed oil, rice oil, maize germ oil, peach-kernel oil, coffee oil, Jojoba oil, sunflower oil, thistle oil, cocoa butter or the like, or the hydrated, polyoxyethylated, polyoxy- or hydrated polyoxyderivatives or fractionated derivatives thereof, can also be employed.

Preferably, the oily component is a mixture of two or more of these oil or their derivatives. Preferably, the oily component is sesame oil.

According to certain embodiments of the present invention, the oily component can be a plant oil as set forth in the foregoing description. This plant oil can be selected from oils derived from the plant of *Perilla* spp. (e.g. *Perilla frutescens* which is also known as *perilla*, Chinese basil, beefsteak, etc), *Nigella* spp. (e.g. *Nigella sativa* which is also known as black cumin, black caraway or fennel seed), *Urtica* spp. (e.g. nettle), *Astragalus* spp. (e.g. milk vetch), *Petasites* spp. (e.g. butterbur), *Citrus* spp. (e.g. lemon), *Uncaria* spp. (e.g. Cat's claw), *Lavandula* spp. (e.g. lavender), *Mentha* spp. (e.g. peppermint), *Eucalyptus* spp. (e.g. *Eucalyptus globulus* which is also known as Tasmanian blue gum, southern blue gum or blue gum), *Matricaria* spp. (e.g. German chamomile), *Rosmarinus* spp. (e.g. rosemary), *Curcuma* spp. (e.g. turmeric), *Allium* spp. (e.g. garlic), or a combination of any two or more thereof.

In certain embodiments, the oily component comprises or is plant oil derived from the plant of *Perilla* spp. and/or *Nigella* spp.

The anti-allergic oil derived from plant is suitable to be used in the preparation as it contains a high content of oily component and able to function as an integral component of the barrier, apart from being able to provide an anti-allergy effect. Furthermore, these plant oils are theoretically interchangeable with the oily component as set forth in the foregoing description to form the physical gel barrier.

Further examples of oily components that can also be of use according to the embodiment of the present invention are animal oils, saturated or non-saturated esters, higher alcohols and/or silicone oils, or mixtures of two or more of these components. To reinforce the retention on the mucous membranes, waxes, together with one or more oils such as those defined hereinbefore, may also be used to form part of the oily component. The examples of suitable wax include carnauba wax, *Cera alba*, *Cera flava*, *Cera chinesis*, *Cera japonica*, Candelilla wax, microcrystalline wax, wool wax and okozerite.

Individually, each type of oil as set forth in the preceding description may contribute to the thixotropic properties of the finished formulation as the oily component. However, each oil has its unique specifications in terms of odour, appearance, specific gravity at 20 CC, saponification value, refractive index, and fatty acid composition. Due to the differences in chemical and physical characteristics (especially fatty acid compositions), the natural seed oils (*perilla* and *nigella* seed oils), when used at the optimal ratios, are considered modulators of the thixotropic formulation, as they are able to alter the finished formulation's specifications such as viscosity, density, uniformity of mass, which would ultimately affect the product's performance and efficacy. For example, viscosity will affect the product's speed or rate in forming the impermeable protective barrier upon application; whereas density and uniformity of mass will affect the distribution and spray pattern of the product during application into nasal cavity.

The oily component has for preference a proportion by weight in the finished preparation (i.e., the nasal or pharmaceutical composition) from about 10% to about 80%, in particular from about 40% to about 70%, or from about 10% to about 60%, or from about 10% to about 50%, or from about 10% to about 40%, or from about 10% to about 30%, or from about 10% to about 25%.

The anti-allergic oil has for preference a proportion by weight in the finished preparation (i.e., the nasal or pharmaceutical composition) from about 10% to about 80%, in particular from about 40% to about 70%, or from about 10% to about 60%, or from about 10% to about 50%, or from about 10% to about 40%, or from about 10% to about 30%, or from about 10% to about 25%.

In accordance with a preferred embodiment of the present invention, the anti-allergic oil and the oily component can be present in a weight ratio range of 1:10 to 10:1, for example, from about 1:9 to about 9:1, or from about 1:8 to about 8:1, or from about 1:7 to about 7:1, or from about 1:6 to about 6:1, or from about 1:5 to about 5:1, or from about 1:4 to about 4:1, or from about 1:3 to about 3:1, or from about 1:2 to about 2:1, or about 1:1.

In certain embodiments of the present invention, the nasal composition can contain *perilla* oil as the anti-allergic oil and sesame oil as the oily component of the oil-based barrier-forming preparation. The weight ratio of the *perilla* oil to sesame oil can be in the range of about 1:10 to 10:1, for example, from about 1:9 to about 9:1, or from about 1:8 to about 8:1, or from about 1:7 to about 7:1, or from about 1:6 to about 6:1, or from about 1:5 to about 5:1, or from about 1:4 to about 4:1, or from about 1:3 to about 3:1, or from about 1:2 to about 2:1, or about 1:1. In certain embodiments, the weight ratio of the *perilla* oil to sesame oil is in the range of about 1:3 to 3:1.

Preferably, the total proportion of oils (anti-allergic oil and the oily component) in the nasal composition can be in the range of about 10-80% by weight of the composition, or from about 20-80% by weight, or from about 30-70% by weight, or from about 30-60% by weight, or from about 35-55% by weight, or from about 40-55% by weight, or from about 40-50% by weight of the composition.

Surprisingly the mixture of oils (anti allergic oil and oily component) leads to an improved spray pattern. This improved spray pattern gives a more even film formation in nasal application and ultimately provides better protection against allergens.

The second component of the oil-based barrier-forming preparation of the composition is the gel former(s) for a gel, for example, a thixotropic gel. In certain embodiments, a thixotropic gel provides the effect of creating suspensions, which may lend the preparation thixotropic properties.

The gel formers for thixotropic gel can be selected from the group consisting of organic suspension media and inorganic suspension media, or a combination thereof. The organic suspension media can be: (i) polysaccharides, in particular cellulose (in particular microcrystalline cellulose, such as Avicel® (FMC Corporation, Philadelphia, USA) or cellulose derivatives, such as carboxymethyl cellulose or the salts thereof (in particular alkaline metal salts, such as sodium salts), alone or in mixtures with microcrystalline cellulose, methylcellulose, guar gum, tragacanth or dextrine esters; (ii) polymer compounds which do not belong to the polysaccharides, in particular polyvinyl alcohols, polyacrylates, such as polyacrylic acid or polymethacrylate (cross-bonded in particular), polyacrylate block copolymers with alternating hydrophilic and hydrophobic blocks, such as, in particular, Hypane hydrogels (Kingston Technology Inc., N.Y., USA); or (iii) other organic gel formers, such as oxyethylenated (=polyoxyethylenated) polyol fatty acid esters, in particular alkyl-(especially methyl-) monosaccharide-$C_6$-$C_{24}$ fatty acid esters, or mixtures thereof (alone or in mixtures with appropriate non-oxyethylenated polyol-fatty acid esters, in particular methyl-monosaccharide-$C_6$-$C_{24}$ fatty acid esters, or methylglucoside-sesquistearate (=mixture of the mono and distearate), or oxyethylenated with ethylene oxide, preferably in an amount of 2 to 50, or in particular 20 mol, with 20 mol ethylene oxide added, available for example under the brandname "Giucamate SSE 20®" from Amerchol Corp. (Du Pont, Edison, N.J., USA; CAS No. 68389-70-8) or a mixture thereof with methylglucoside-sesquistearate (available for example under the brandname "Giucamate SSE 20®" (Amerchol; CAS No. 68389-70-8). Preferably, this is mixed in the proportion by weight of 10:1 to 1:10, in particular from 3:1 to 1:3, e.g. of 1:1; others are the mixtures of metal salts of phosphoric acid diesters and organopolysiloxanes, which are derivatised with a polyvalent metal salt of a phosphoric acid diester containing silicon.

On the other hand, the inorganic suspension media that can be used as gel former for thixotropic gel includes, kaolin clays forming colloids, in particular (especially hydrated) metal oxide silicates, such as bentonite, or (for preference highly dispersed colloidal) silicon dioxide in dried or, for preference, hydrated form, three-layer clay materials such as smectite, in particular synthetic smectites with triochahedric coordinated cations, manufactured from magnesium silicates and alkali cations, or suitable colloidal magnesium to aluminium silicates; or synthetic hectorite clays such as Laponite® (Laporte, London, Great Britain); or mixtures of two or more of these components.

According to one of the preferred embodiments of the present invention, the organic gel formers as set forth under (iii) are to be used as the gel formers for thixotropic gel of the nasal composition.

Preferably, the nasal composition of the present invention can contain xanthan gum and/or bentonite as the main gel-forming components for the thixotropic gel, and glycerol monostearate as the emulsifier for the thixotropic gel.

The gel formers are present for preference in a proportion by weight, related to the finished preparation, from about 0.1 to 15% by weight, for preference (in particular in the case of organic gel formers) from about 0.2 to 10% by weight, such as, about 0.2 to 8% by weight, or about 0.2 to 6% by weight, especially, from about 0.25 to 4% by weight of the preparation.

A general advantage of a thixotropic gel is its easy use, for example, in contrast to thermosensitive gel, it does not require any defined temperatures before administration. A simple shaking of the preparation allows the gel to set into the sol state appropriate for administration.

The third component of the oil-based barrier-forming preparation is an aqueous base. This aqueous base can be water, or water with stabilising additives. As an aqueous basis, water is particularly suitable, to which other water-soluble components can be added. The water-soluble components added can be a stabilising additive, in particular ethylene glycol, 1,2 propylene glycol, a sugar alcohol such as sorbite, hexite, or mannite, or in particular glycerine, which are capable of supporting and stabilizing the formation of the gel. The water, with or without the stabilising additives, can be added to the preparation as the aqueous basis as such, in mixture with other constituents of a preparation according to one of embodiments of the invention, or as a constituent of the finished preparation.

Water is present for preference in a proportion of about 10 to 80%, for preference from about 30 to 70%, more preferably about 40 to 60% by weight, of the finished preparation. The stabilising additives may be contained in the water-soluble component in the form of one or more di- or polyols, especially glycerine, in a quantity ranging from, for preference, about 0.1 to 10% by weight of the finished preparation, respectively. The water proportion is suitable in particular for regulating the basic viscosity of the thixotropic gel. The stabilising agent, such as glycerine, can also be used as an excipient for the preparation.

In certain embodiments, the oil-based barrier-forming preparation of the nasal composition is an oil-in-water emulsion or microemulsion.

The preparations can be manufactured according to conventional and known methods, which include in particular the mixing of the components, if required step by step and/or under movement and/or heating of the fluid, for example by stirring. A start is made for preference with sterile initial components and work is carried out under sterile conditions; incomplete interim stages, which do not contain all the components, are sterilised. At the end of the process, the preparations can be subjected to a further sterilisation procedure by suitable usual methods, if required.

The determination of the thixotropy may be effected as described above, and a check can therefore easily be carried out as to whether the mixtures manufactured with the above components fall among the thixotropic gels to be used according to particularly advantageous embodiments of the present invention. The enumeration of the three components in the oil-based barrier-forming preparation upwards or downwards is not to be understood such that these components must be added one after another in sequence, and in particular not that water and the additives are mixed separately. In fact, the components can be mixed in any conceivable sequence, in particular the customary sequence and manner, for the manufacture of preparations according to the embodiment of the present invention.

The nasal composition can be prepared in the form of a nasal spray. In more particular, the thixotropic gels can be formulated as nasal drops (usually in bottles with pipettes) or, for preference, as nasal sprays. An example of the nasal spray product formulation according to a preferred embodiment of the present invention is further detailed in Example 1.

According to a preferred embodiment of the present invention, a portable spray device can be used for the nasal spray. The portable spray device (or nasal dispenser) can be activated manually by finger pressure. Examples of suitable spray device can be those comprising a storage container, a spray pump, and for preference means for nebulization. It is also preferable for the spray device to contain loose stirring elements, such as small metal pellets or rods, which contribute to the shaking up effect. The spray device can also contain both distribution pump as well as simple squeeze bottles in combination with a storage container, or a pre-compression pump. The suitable pump can be the VP7/1 OOS pump (Perfect Valois VP7) from Valois SA, France, and the "3-K Pumpe" (3-K Pump) or the COMOD system or the AP3 pump from Aero Pump GmbH, Hofheim/Taunus, Germany. For preference, the dosage unit of a spray device amounts to about 1 to 50 ml. In the case of portable storage containers for nasal sprays, it is preferable to have a dosage unit of about 3 to 40 ml, in particular about 5 to 35 ml.

According to one of the preferred embodiments of the present invention, the present invention pertains to an optionally thixotropic nasal preparation contained inside a portable spray device as described in the foregoing description.

Besides the enhanced barrier function of the nasal composition, sprayability of the composition can also be measured using a standard sprayability test, as further detailed in Example 2. The spray pattern of different combination of anti-allergic oil and the oily component is further shown in FIGS. 1A-1E.

When the nasal composition is administered into the nasal cavity, the sprayed droplets will come into contact with the nasal mucosa to form the gel barrier on the surface. The coverage of the gel barrier formed depends on the spray pattern and the location where the droplets come into contact with on the nasal mucosa surface. As a result, the spray patterns of the nasal composition can directly impact on the products' efficacy by influencing the formation and coverage of the gel barrier on nasal cavity. Taking into account the cone-shaped and tunnel-like structure of the human nasal cavity, a desirable spray pattern for the nasal composition would be of an annular shape, with a relatively large annular width and a small hollow substantially at the centre of the spray pattern, which could then be transformed into cone-shaped and tunnel-like distribution of droplets, that can create a gel barrier that covers substantially the entire surface area of the nasal cavity providing a substantially complete coverage to the nasal cavity against airborne allergens, yet leaving a small hollow centre to avoid the solution from directly blocking the airway and minimizing any unpleasant feeling of a blocked airway. Preferably, the area of coverage of the spray pattern formed in the nasal cavity is in a range of about 70% and 95%.

Preferably, the nasal composition can provide a substantially annular spray pattern, with an annular ring width range of about 0.5 cm to 12.0 cm, with a distance between an origin of spray to an impinged surface of about 0.1 cm to 10.0 cm. In certain embodiments, the substantially annular spray pattern has an annular ring width range of 0.5 to 12.0 cm, with a distance between an origin of spray to an impinged surface 10.0 cm. In certain embodiments, the substantially annular spray pattern has an annular ring width of at least 2.5 cm, for example, at least 3.0 cm, or at least 3.5 cm, or at least 4.0 cm. In certain embodiments, the annular ring width is no more than about 12.0 cm, for example, no more than about 10.0 cm, or no more than about 8.0 cm, or no more than about 6.0 cm.

Theoretically, the annular ring width of the spray pattern is proportional to the distance between the origin of spray to the impinged surface, i.e. the greater the distance, the greater the diameter of the spray pattern. The examples of the spray pattern of the nasal composition as shown in the sprayability test in Example 2 were obtained with a distance between the origin of spray to the impinged surface of approximately 7 cm. In certain embodiments, the largest diameter of the spray pattern is from about 2 cm to about 15 cm, for example, from about 5 cm to about 10 cm. In such embodiments, the unit dose per spray may be from about 120 μl to about 160 μl.

As set forth in the preceding description, the anti-allergic oil and the oily component can be present in a weight ratio range of about 1:10 to 10:1 in a nasal spray composition. In a preferred embodiment of the present invention, the anti-allergic oil is *perilla* oil and the oily component is sesame oil. Preferably, the desired spray pattern can be obtained by the specific combination ratio of these oils in a weight ratio range of about 1:3 to 3:1. More preferably, the *perilla* oil and the sesame oil is used in a weight ratio of about 1:1 in the nasal spray composition. However, other combinations of oils in other combination ratios that are capable of providing the preferred annular spray pattern can also be applied in the present invention.

According to a second aspect, there is provided a pharmaceutical composition comprising a composition according to the first aspect and a pharmaceutically acceptable carrier, excipient, diluent and/or additive. The pharmaceutically acceptable carrier, excipient and/or diluent for use in the pharmaceutical composition can be selected from the group consisting of binders, surfactants, preservatives, colourants, flavouring substances, pH regulators, regulators of the osmotic activity and salt-forming groups.

The binders (in addition to the gel formers) used in the nasal composition of the present invention may be, for example, dextrines, hydroxypropyl cellulose, hydroxypropylmethyl cellulose, polyvinyl pyrrolidone, gelatines, pectin, starch, or also sodium carboxymethyl cellulose. According to certain embodiments of the present invention, the binder can also provide further gel-forming properties. The binders may be present in proportions of, for preference, up to about 10% by weight, or up to about 5% by weight, for preference from about 0.1 to 3.0% by weight of the finished preparation.

Surfactants may be present in the preparation in quantities of up to about 2% by weight, for example from about 0.2 to 0.8% by weight. The surfactants can be anionic, cationic, non-ionic, zwitterionic or amphoteric detergents. For instance, the suitable anionic detergents can be sulphonates, e.g. alkylbenzol sulphonates, alkanesulphonates, Alta-olefin sulphonates, 2-acyloxy-alkan-1-sulphonates, or fatty acid monoglyceride sulphates, sulphates, e.g. alkyl sulphates, polyoxyethyl sulphates, fatty acid monoglyceride sulphates, or the salts thereof (e.g. with alkali metals, ammonia or ammonium compounds) can be used in the composition. Examples of suitable cationic detergents include quaternary ammonium compounds, e.g. alkylaryiether dimethylbenzalkonium halogenides, alkyltrimethyl ammonium chlorides, alkyldimethyl ethylammonium halides, alkylpyridinium halogenides, alkyldimethyl ethylammonium halides, alkylpyridinium halogenides, alkylimidazolium halogenides, alkyldimethyl dichlorobenzyl ammonium halogenides, acylcolamonoformylinether pyridinium halogenide or alkylarylmethyl pyridinium halogenides. Examples of non-ionic detergents include polyethylene oxide condensates of alkylphenolene, ethylene oxide condensation products, derived from the reaction of ethylene oxide with the product from propylene oxide and ethylenediamine, the condensation products of aliphatic alcohols with ethylene oxide, or amide detergents which contain an ammonium, monoethanolamino, diethanolamino, or other alkanolamide group. Examples of zwitterionic detergents include aliphatic quaternary compounds containing ammonium and phosphonium or sulphonium groups. Examples of suitable amphoteric detergents include aliphatic secondary or tertiary amines.

Preservation agents are in particular complex formers, such as ethylenediamine tetraaceticacid, antioxidants such as ascorbic acid, butylated hydroxyanisol (BHA) or butylated hydroxytoluene (BHT) or other preservation agents such as methyl, ethyl, propyl, or butyl esters of 4-hydroxybenzoic acid (Parabene), benzoic acid, cetrimide, cetyltrimethyl ammonium chloride, sorbinic acid or thiomersal, or the like. Preservation agents may be present, for example, in weight proportions (related to the finished preparation) of up to about 5% by weight, and in particular in the range from about 0.5% to 3.5% by weight. Preferably, preservation agents are omitted in order to avoid negative effects on the self-purifying mechanisms of the nasal mucosa. Preferably, the preservation agent used in the present invention can be ethylendiaminetetraacetic acid (EDTA), chlorhexidine, benzalkonium chloride, phenoxyethanol, phenylethyl alcohol, caprylyl glycol, ethylhexylglycerin, parabens, potassium sorbate, sodium benzoate or polyhexanide. Additionally, tocopherol can be used as an anti-oxidant, which is useful in preventing and/or reducing rancidity of the composition that may occur, and thus prolonging the shelf life of the product.

As colouring agents, use may be made, for example, of toxicologically acceptable substances such as betaceratin, Erythrosin, Gelborange S, Indigotin, or Tartrazin. By the addition of colouring agents, can be examined, for example, to determine whether the preparations according to the invention are distributed over the entire nasal mucous membrane. Colouring agents may be present, for example, in the weight proportions (related to the finished preparation) of up to about 1% by weight, and in particular from about 0.001% to 0.200% by weight.

Flavouring substances are for preference not among the flavouring substances which belong to the etheric oil or plant extracts, but such as fruit flavouring substances (e.g. fruit esters) or vanillin, which may be present, for example, as up to about 1% by weight of the finished preparation, and in particular between about 0.001% and 0.500% by weight.

As pH regulators, use may be made of buffer additives, e.g. phosphate buffers or buffers on a citric acid basis. For preference these serve to adjust the pH value to between 3 and 9, and in particular between 5 and 8, and may be present in concentrations of up to, in particular, less than about 120 mM, for example about 20 to 100 mM. Preferably, the buffering agent used in the present invention is monopotassium phosphate and/or dipotassium phosphate.

As regulators of osmotic activity, use may be made, for example, of sugars or sugar alcohols (which can be used at the same time as additives) or, in particular, sodium chloride, for example (in particular for sodium chloride) in a concentration of up to about 0.9% (% by weight).

If salt-forming groups (anionic, such as carboxy, sulphonyl, or sulphate) or cationic groups (such as amino) are present in the components or active substances referred to above, they may be also be present (in whole or in part) as (especially pharmaceutically acceptable) salts, in the case of anionic groups, for example, as alkali metal salts, alkaline-earth metal salts, ammonium salts, zinc salts, or tin salts, and in the case of cationic groups, for example as salts of organic or inorganic acids, such as of hydrogen halides hydrocarbons, sulphuric acid, phosphoric acid, organic sulphones or sulphates or carboxylic acids, such as acetic acid, or, if both anionic and cationic groups are present, as inner salts.

In accordance with certain embodiments, the excipients used in a nasal spray composition of the present invention can contain a buffering agent such as glycerine, monopotassium phosphate and/or dipotassium phosphate, an antioxidant such as tocopherol, a preservation agent such as EDTA, chlorhexidine, benzalkonium chloride, phenoxyethanol, phenylethyl alcohol, caprylyl glycol, ethylhexylglycerin, parabens, potassium sorbate, sodium benzoate or polyhexanide, and a solvent such as water.

The nasal composition according to the first aspect or a pharmaceutical composition according to the second aspect of the invention can further comprise an anti-allergic drug or pharmaceutically active anti-allergic substance, for example an antihistamine or an additional mast cell stabilizer (e.g. cromoglicate, etc). In certain embodiments, the nasal composition or the pharmaceutical composition can further comprise an antihistamine, including $H_1$-antihistamine (e.g. azelastine, olopatadine, triprolidine, bilastine, cetirizine, pyrilamine etc), $H_2$-antihistamine (e.g. cimetidine, famotidine, etc) and $H_3$-antihistamine (e.g. thioperamide etc). The antihistamine opposes the activity of histamine receptors in a subject and further enhances the inhibitory effect of mast cell activation of the anti allergic oil and oily component (e.g. *perilla* oil and sesame oil) in the nasal composition or the pharmaceutical composition. In certain embodiments, azelastine can be used as the antihistamine in the composition of the invention, as it has a triple mode of action, i.e. antihistamine effect, mast cell stabilizing effect and anti-inflammatory effect. For example, the nasal composition or the pharmaceutical composition may comprise from about 0.1 wt. % to about 50 wt. %, or from about 0.01 wt. % to about 10 wt. %, or from about 10 wt. % to about 40 wt. %, or from about 20 wt. % to about 30 wt. % of antihistamine by weight of the composition of the invention described herein.

The person skilled in the art is aware, or can determine in a simple experimental manner, which of the components referred to can be combined with one another to form a preparation according to the invention, without mutually negative influences arising (precipitation, absence of thixotropic properties, or the like).

According to a further aspect, there is provided a nasal composition according to the first aspect or a pharmaceutical composition according to the second aspect for use in a therapeutic method of inhibiting mast cell activation (mast cell stabilization). The method may, for example, comprise contacting the mast cells with the nasal composition according to the first aspect or the pharmaceutical composition according to the second aspect.

Mast cells are activated by allergens through cross-linking with IgE receptors on the surface of the cells, by physical injury through damage-associated molecular pattern molecules, by pathogen-related agents through pathogen associated molecular pattern molecules, by various compounds with their associated G-protein coupled receptors and/or by complement proteins. Activation of a mast cell causes a complex intracellular signalling pathway to occur, which results in degranulation of the mast cells. This is where molecules stored in the granules of the mast cell are released outside of the cell. This includes, for example, serine proteases (e.g. tryptase), histamine, serotonin and proteoglycans (e.g. heparin). Inhibiting activation of mast cells may, for example, include any one or more of these steps. For example, the compositions disclosed herein may be useful in inhibiting mast cell degranulation. For example, the compositions disclosed herein may be useful in inhibiting release of histamine from the mast cell.

The nasal composition according to the first aspect or pharmaceutical composition according to the second aspect may, for example, reduce histamine release by at least about 20%. For example, the nasal composition or pharmaceutical composition may reduce histamine release by at least about 30%, for example at least about 40%, for example at least about 50%, for example at least about 60%, for example at least about 70%, for example at least about 75%, for example at least about 80%, for example at least about 85%, for example at least about 90%, for example at least about 95%. For example, the nasal composition or pharmaceutical composition may reduce histamine release by up to 100%, for example up to 99%, for example up to 98%.

According to further aspects, there is provided a nasal composition according to the first aspect or a pharmaceutical composition according to the second aspect for use in preventing and/or treating a disorder of the nasal cavity associated with mast cell activation and/or mast cell degranulation.

According to a further aspect, there is provided a nasal composition according to the first aspect or a pharmaceutical composition according to the second aspect for use in preventing and/or treating allergic disorders of the nasal cavity, including seasonal allergic rhinitis and perennial allergic rhinitis.

The nasal composition according to the first aspect or pharmaceutical composition according to the second aspect may, for example, reduce histamine concentration in the tissue of a subject by at least about 20% following administration of the nasal composition or pharmaceutical composition respectively. For example, the nasal composition or pharmaceutical composition may reduce histamine concentration in the tissue of the subject by at least about 30%, for example at least about 40%, for example at least about 50%, for example at least about 60%, for example at least about 70%, for example at least about 75%, for example at least about 80%, for example at least about 85%, for example at least about 90%, for example at least about 95% following administration of the nasal composition or pharmaceutical composition respectively. For example, the nasal composition or pharmaceutical composition may reduce histamine concentration in the tissue of a subject by up to 100%, for example up to 99%, for example up to 98% following administration of the nasal composition or pharmaceutical composition respectively. According to one of the embodiments, the reduction of histamine release is expected to occur for approximately 4-6 hours after administration of the nasal composition.

Histamine concentration in the tissue of a subject may be measured by any method known to a person skilled in the art. For example, histamine concentration may be determined by microdialysis sampling followed by quantification with commercially available ELISA kits or by HPLC. For example, histamine concentration at a localised site may be determined using tissue samples such as tissue homogenates. For example, histamine concentration may be determined using a nasal tissue where an allergen has come into contact with mast cells (e.g. skin or nasal lining).

According to a third aspect, there is provided a nasal composition according to the first aspect or a pharmaceutical composition according to the second aspect for use in preventing and/or treating allergic disorders of the nasal cavity, including seasonal allergic rhinitis and perennial allergic rhinitis.

Use for the manufacture of a product for the therapeutic treatment of nasal disorders comprises in particular the appropriate procurement of the product (e.g. as a pharmaceutical product in the broader or narrower sense); in other words, the manufacture of the preparation, its introduction in particular into the spray device, its packing, and the corresponding provision of instructions for use in therapeutic treatment, for example by way of a package insert and/or printings on the package.

The composition is useful in preventing and/or treating allergic disorders of the nasal cavity as it is able to form a mechanical barrier on nasal mucosa, which is impermeable to common allergens such as pollens, animal dander and dust mite. The barrier formed due to the thixotropic properties of the emulsion contains mucoadhesive gel-forming ingredients (such as xanthan gum and bentonite) and emulsifier (glycerol monostearate). This impermeable gel layer can block the contact between incoming allergen particles and the nasal mucosa, thereby preventing the trigger of allergic reaction and stopping the onset of allergic rhinitis symptoms. Relief of the symptoms can last for several hours as long as the gel layer is retained on the nasal mucosa surface.

The addition of the anti-allergic oil into the oil-based barrier-forming preparation is capable of altering the physical and chemical properties of the composition, such as an optimal viscosity which allows the composition to be evenly dispersed through a spray head. This would result in a spray pattern, as set forth in the preceding description that can fully and evenly coat the nasal cavity, providing complete blockage of incoming allergens to nasal mucosa. Such sprayability properties of the composition thus results in better physical protection as well as overall efficacy in the therapeutic and preventive effects against nasal disorders caused by allergens, such as allergic rhinitis.

According to a further aspect, there is provided a therapeutic method for inhibiting mast cell activation. The method may, for example, comprise contacting the mast cells with the nasal composition according to the first aspect or the pharmaceutical composition according to the second aspect.

According to a further aspect, there is provided a method for preventing and/or treating allergic disorders of the nasal cavity, including seasonal allergic rhinitis and perennial allergic rhinitis, in a subject comprising administering to the subject an effective amount of a nasal composition according to the first aspect or a pharmaceutical composition according to the second aspect.

Administration can be effected in any desired manner. In the case of nasal administration, the quantity suitable for treatment of the disorders referred to, administered per spray burst, in particular the quantity of the preparation released with a nasal spray per spraying action, wherein 1 spray burst is approximately between about 3 and 200 µl, and in particular between about 50 and 150 µl, e.g. approximately 140 µl per spray. In one of the embodiments, the quantity suitable for treatment of a disorder is approximately 1-2 sprays per nostril, or subject to the prescription by a healthcare professional.

Administration takes place once or for preference several times daily, in particular at intervals of a few hours, for example at intervals of about 1 to 8 hours, and in particular of about 4 to 6 hours; for preference starting directly after waking, and, if protection is also required at night, for the last time immediately before going to sleep. For preference, treatment during night time can be included for perennial allergy.

A nasal spray, which is used for preference several times a day, in particular beginning shortly after waking and last used immediately before going to sleep, at intervals of several hours, in particular from about 1 to 8 hours, for preference from about 4 to 6 hours, and for preference in a volume of between about 3 and 500 µl, in particular between about 50 and 150 µl, per nostril.

In certain embodiments, the subject is a human. Besides being useful for human applications and treatments, the present invention is also useful in a range of mammals, which can also be affected by nasal disorder. Such mammals include non-human primates (e.g. apes, monkeys and lemurs), for example in zoos, companion animals such as cats or dogs, working and sporting animals such as dogs, horses and ponies, farm animals, for example pigs, sheep, goats, deer, oxen and cattle, and laboratory animals such as rodents (e.g. rabbits, rats, mice, hamsters, gerbils or guinea pigs).

According to the further aspect, there is provided the use of an anti-allergic oil derived from plant and an oil-based barrier-forming preparation in the manufacture of a medicament, pharmaceutical composition, or nasal composition. The medicament, pharmaceutical composition or nasal composition may, for example, be used for preventing and/or treating allergic disorders of the nasal cavity, including seasonal allergic rhinitis and perennial allergic rhinitis.

EXAMPLES

Example 1: Nasal Spray Formulation

| Ingredient | Percentage (%) by weight |
|---|---|
| Bentonite veegum | 0.8 |
| Xanthan gum | 0.2 |
| Monopotassium phosphate | 0.28 |
| Dipotassium phosphate | 0.08 |
| Glycerin anhydrous | 0.53 |
| Glycerol monostearate | 0.25 |
| *Perilla* seed oil | 22 |
| Sesame seed oil | 22 |
| Spearmint oil | 0.1 |
| Mixed tocopherols | 0.5 |
| Potassium sorbate | 0.2 |
| Phenoxyethanol and caprylyl glycol | 2 |
| Purified water | 51.06 |

Example 2: Sprayability and Spray Pattern Test

Figure 2:
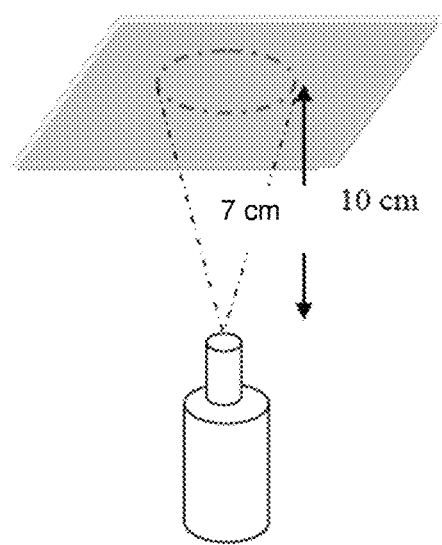
FIG. 2 is a schematic representation of the apparatus setting for the sprayability test of a nasal spray composition as described in one of the preferred embodiments of the present invention.

The sprayability test was conducted using 5 different samples of the nasal spray with different ratios of the anti-allergic oil (*perilla* oil) and the oily component (sesame oil): (a) sesame oil only, without anti-allergic oil; (b) *perilla* oil and sesame oil in a weight ratio of 1:3; (b) *perilla* oil and sesame oil in a weight ratio of 1:1; (b) *perilla* oil and sesame oil in a weight ratio of 3:1; and (e) *perilla* oil as both the anti-allergic oil and the oily component. Prior to testing, 5 sprays were released. A 10×10 cm black carton was fixed onto a 10×10 cm glass plate and held perpendicularly to the spraying direction of the nasal spray, with the spray device (HDPE bottle, with AP3 spray head from Aero Pump GmbH) located at a distance of 7 cm from the black carton/glass plate, as shown in FIG. 2. One complete dose of 140 µl was sprayed onto the glass plate. For each product, the spray pattern was described and quantified. The time for releasing one single dose of the container was less than 1 second. The testing was repeated 3 times for conformation of the result.

Example 3: Quantification of Spray Pattern

The spray patterns of 5 different samples of the nasal spray with different ratios of the anti-allergic oil (*perilla* oil) and the oily component (sesame oil) as obtained by Example 2 were analysed to compare the sprayability of the respective samples. All measurements were recorded to the closest 0.5 cm. The spray patterns of the samples (a)-(e) are further described as follows: (a) annular shape with a ring width of 2.5 cm, and a relatively large hollow centre; (b) annular shape with a ring width of 4 cm, and a relatively moderate-sized hollow centre; (c) annular shape with a ring width of 4.5 cm, and a relatively small hollow centre; (d) annular shape with a ring width of 3.5 cm, and a relatively moderate-sized hollow centre; (e) annular shape with a ring width of 2 cm, and a relatively large hollow centre.

The observed spray patterns for formulations that contain sesame oil and *perilla* oil in combinations, either in the weight ratio of 1:3, 1:1 or 3:1 (samples (b)-(d)), are surprising. For these formulations, a wide, spread out spray pattern with a small to moderate hollow centre was observed. As the spray pattern of the sample having only sesame oil (sample (a)) and sample having only *perilla* oil (sample (e)) gave spread out spray pattern that has a big hollow centre, the spray patterns of the nasal compositions having combination of sesame oil and *perilla* oil were unexpected.

Example 4: In Vitro Testing of Mast Cell Line HMC-1

Mast cell lines, i.e. HMC1 cells (provided by Dr Joseph H. Butterfield; Mayo Clinic, Rochester, Minn., USA), were cultured in Isocove's Modified Dulbecco's Medium (IMDM) containing 10% Fetal Bovine Serum (FBS), 2 mM L-glutamine, 50 µM 2-mercaptoethanol, 100 U/mL penicillin and 100 µg/mL streptomycin. Cells were maintained at 37° C. in 5% $CO_2$ in a humidified atmosphere.

Percentage of living cells was determined by trypan blue staining. A 1:10 dilution with 50 µl cell suspension and 450 µl trypan blue was prepared and the number of living and dead cells was counted in a hemocytometer. $10^6$ living cells were transferred into safe-lock Eppendorf tubes. Cell suspensions were centrifuged (200 g, 5 min) and supernatant was discarded.

The effect of *perilla* oil, sesame oil and a combination of *perilla* oil and sesame oil (in a combination ratio of 1:1) in the vehicle Kolliphor ELP (polyoxyl-35 hydrogenated castor oil) was determined. The positive control Cromolyn in phosphate buffer saline (PBS), the vehicles PBS and ELP, and calcium ionophore A23187 were also tested as controls.

After adding 100 µl IgE (100 ng/ml in PBS/ELP) to the cell pellets, cells were incubated for 12 hours over night, at 37° C. Cells were than incubated for 2 hours, at 37° C. with different concentrations of compounds. After centrifugation (200 g, 5 min), supernatant was discarded and cell pellet was again incubated for 1 hour, at 37° C. with 100 µl anti-IgE (1 µg/ml in PBS/ELP). For the final incubation time of 6 hours, at 37° C., 300 µl HMC1 media was added. Cells were again centrifuged (200 g, 5 min) and supernatant was collected and stored as 300 µl aliquots at −20° C. for ELISA measurements. Cell pellets were resuspended in 100 µl HMC1 media for determining cell viability.

The procedure was slightly different when the compound testing was calcium ionophore A23187. After adding calcium ionophore (100 µg/ml) to the cell pellets, cells were incubated for 30 min, at 37° C. For the final incubation time of 6 hours, at 37° C., 300 µl HMC1 media was added. Cells were again centrifuged (200 g, 5 min) and supernatant was collected and stored as 300 µl aliquots at −20° C. for ELISA measurements. Cell pellets were resuspended in 100 µl HMC1 media for determining cell viability.

The concentration of histamine in the collected supernatant was determined by ELISA, using a kit obtained from IBL International according to the manufacturer's guidelines. Each sample was measured twice. Due to expected measuring limits, vehicle (PBS, ELP) treated samples were diluted 1:2 and calcium ionophore treated samples were diluted 1:5.

Statistical analysis was performed with GraphPad Prism (Version 5.01) software (GraphPad Software Inc., San Diego, Calif., USA) using the unpaired two-tailed Students t test. A P value of less than 0.05 was considered statistically significant.

Figure 3:
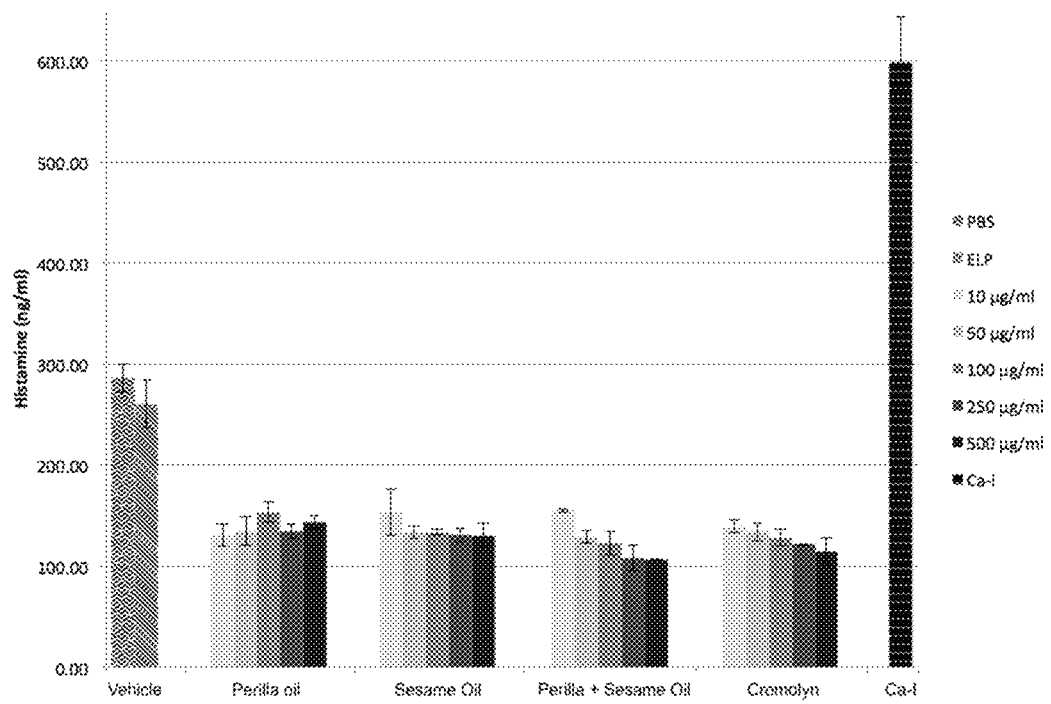
FIG. 3 is a graph showing histamine release after treatment with various compounds.

The results are shown in FIG. 3 below.

As anticipated, treatment with only IgE/anti-IgE (negative control) and calcium ionophore showed the highest values of histamine production. Calcium ionophore samples released all histamine since the cells were completely destroyed by this treatment.

Histamine levels were significantly reduced in all compound treated samples and in cromolyn treated samples compared to PBS and ELP controls. Treatment with *perilla* oil or sesame oil alone shows an unspecific reduction since no dose-dependency could be observed. Treatment with a combination of *perilla* oil and sesame oil or treatment with cromolyn showed a specific, dose-dependent decrease of histamine release. Decreased histamine release is indicative of inhibition of mast cell activation/mast cell stabilization.

Comparing the average histamine release of individually treated *perilla* oil and sesame oil to the average histamine release of the combination of *perilla* oil and sesame oil, the combination showed significantly reduced histamine release at 250 µg/ml and 500 µg/ml (p=0.0185 and p=0.0092 respectively). This is comparable to cromolyn. The combination of *perilla* oil and sesame oil thus works synergistically to inhibit histamine release.

The invention claimed is:

1. A nasal composition comprising:
   an anti-allergic oil derived from a plant of *Perilla* spp.; and
   an oil-based barrier-forming preparation, wherein the oil-based barrier-forming preparation contains an oily component, one or more gel formers and an aqueous base.

2. A nasal composition according to claim 1, further comprising a further anti-allergic oil derived from the plant of *Nigella* spp., *Urtica* spp. *Astragalus* spp., *Petasites* spp., *Citrus* spp., *Uncaria* spp., *Lavandula* spp., *Mentha* spp., *Eucalyptus* spp., *Matricaria* spp., *Rosmarinus* spp., *Curcuma* spp., *Allium* spp., or a combination of any two or more thereof.

3. A nasal composition according to claim 2, wherein the anti-allergic oil is obtained from the seed, root, leaf, or whole plant parts of the plant.

4. A nasal composition according to claim 1, wherein the oily component is a hydrocarbon, a plant oil, a vegetable oil or hydrated, polyoxyethylated or polyoxy- or hydrated polyoxy or fractionated derivatives thereof, or a combination of any two or more thereof.

5. A nasal composition according to claim 1, wherein the oily component is sesame oil.

6. A nasal composition according to claim 5, which is in a form of a nasal spray.

7. A nasal composition according to claim 1, wherein the anti-allergic oil and the oily component is present in a weight ratio range of about 1:10 to 10:1.

8. A nasal composition according to claim 1, wherein the one or more gel formers are for thixotropic gel and are selected from the group consisting of organic suspension media and inorganic suspension media, or a combination thereof.

9. A nasal composition according to claim 1, wherein the one or more gel formers are for thixotropic gel and contain xanthan gum, bentonite, glycerol monostearate or a combination of any two or more thereof.

10. A nasal composition according to claim 1, wherein the aqueous base is water, or water with stabilising additives.

11. A nasal composition according to claim 1, wherein the oil-based barrier-forming preparation is an oil-in-water emulsion or microemulsion.

12. A nasal composition according to claim 1, which is in the form of a nasal spray.

13. A nasal composition according to claim 12, which provides a substantially annular or circular spray pattern.

14. A nasal composition according to claim 13, wherein area of coverage of the spray pattern formed in a nasal cavity is in a range of about 70% and 95%.

15. A nasal composition according to claim 13, wherein the substantially annular spray pattern has an annular ring width range of about 0.5 cm to 12.0 cm, with a distance between an origin of spray to an impinged surface of about 0.1 cm to 10.0 cm.

16. A pharmaceutical composition comprising a composition according to claim 1 and a pharmaceutically acceptable carrier, excipient, diluent and/or additive.

17. A pharmaceutical composition according to claim 16, wherein the pharmaceutically acceptable carrier, excipient and/or diluent is selected from the group consisting of binders, surfactants, preservatives, colourants, flavouring substances, pH regulators, regulators of the osmotic activity and salt-forming groups.

18. A therapeutic method of inhibiting mast cell activation comprising administering to the mast cells an effective amount of the nasal composition according to claim 1.

19. The method according to claim 18, wherein release of histamine from the mast cells is inhibited.

20. The method according to claim 18, wherein the concentration of histamine in the tissue of a subject is reduced following administration of the nasal composition.

21. The method according to claim 18, wherein the subject has an allergic disorder of the nasal cavity selected from seasonal allergic rhinitis or perennial allergic rhinitis.

22. A method for preventing and/or treating allergic disorders of the nasal cavity, including seasonal allergic rhinitis and perennial allergic rhinitis, in a subject comprising administering to the subject an effective amount of a nasal composition according to claim 1.

* * * * *